United States Patent [19]

Natsugari et al.

[11] Patent Number: 5,198,462
[45] Date of Patent: Mar. 30, 1993

[54] HETEROCYCLIC AMINE, DERIVATIVES, THEIR PRODUCTION AND USE

[75] Inventors: Hideaki Natsugari, Ashiya; Hiroyuki Tawada, Takatsuki; Hitoshi Ikeda, Higashiosaka, all of Japan

[73] Assignee: Takeda Chemical Industries, Ltd., Osaka, Japan

[21] Appl. No.: 777,169

[22] Filed: Oct. 16, 1991

[30] Foreign Application Priority Data

Oct. 16, 1990 [JP] Japan .................................. 2-278038
Sep. 18, 1991 [JP] Japan .................................. 3-237983

[51] Int. Cl.$^5$ ................... A61K 31/38; C07D 335/06
[52] U.S. Cl. ....................................... 514/432; 546/93; 546/101; 546/110; 546/111; 546/142; 546/143; 549/23; 549/26; 549/27; 549/28; 549/404; 549/288; 549/285; 549/280; 514/454; 514/457; 514/458; 514/309; 514/310; 514/455; 514/290
[58] Field of Search ................. 549/28, 288, 404, 285, 549/23, 26, 27, 280; 514/432, 456, 457, 458, 309, 310, 437, 454, 455, 290; 546/141, 143, 142, 93, 101, 110

[56] References Cited

U.S. PATENT DOCUMENTS

| | | | |
|---|---|---|---|
| 3,247,212 | 4/1966 | Johnson | 260/287 |
| 3,594,380 | 7/1971 | Sulkowski | 546/141 |
| 3,798,226 | 3/1974 | Meguro et al. | 514/313 |
| 3,862,152 | 1/1975 | Kuwada et al. | 514/313 |
| 3,870,722 | 3/1975 | Houlihan et al. | 260/283 R |
| 4,078,075 | 3/1978 | Berigen | 514/457 |
| 4,596,822 | 6/1986 | Powers et al. | 514/159 |
| 4,868,210 | 9/1989 | Trivedi | 514/539 |
| 4,994,465 | 2/1991 | Trivedi | 514/539 |

FOREIGN PATENT DOCUMENTS

0326386 8/1989 European Pat. Off. .
0424929 5/1991 European Pat. Off. .
2030675 2/1971 Fed. Rep. of Germany .

OTHER PUBLICATIONS

Chemical Abstracts, vol. 115, No. 15, 1991, 158928m, A. G. Nemazanyi et al.

*Primary Examiner*—Glennon H. Hollrah
*Assistant Examiner*—Mark W. Russell
*Attorney, Agent, or Firm*—Wegner, Cantor, Mueller & Player

[57] ABSTRACT

A novel heterocyclic amine derivative of the general formula:

$$\text{(I)}$$

wherein a ring A and a ring B stand independently for an optionally substituted benzene ring, $Z^0$ stands for O or S or $$\underset{\text{II}}{\overset{Z^0}{\diagup\diagdown}}$$

stands for $-CH_2-$, X stands for O, S or $NR^1$ wherein $R^1$ stands for hydrogen atom or an alkyl group, Y stands for NH, O or $(CH_2)_n$ wherein n denotes 0 to 2, and $R^2$ stands for an optionally substituted hydrocarbon group, or their salts.

20 Claims, No Drawings

HETEROCYCLIC AMINE, DERIVATIVES, THEIR PRODUCTION AND USE

FIELD OF THE INVENTION

This invention relates to novel heterocyclic amine derivatives having excellent activity of inhibiting acyl-CoA:cholesterol acyltransferase (ACAT).

BACKGROUND OF THE INVENTION

As to effectiveness of heterocyclic amine derivatives (e.g. isocoumarin, isoquinolone, benzothiopyran, etc.) for the therapy of arteriosclerosis or for lowering cholesterol in blood, no sufficient study has been conducted.

The present invention principally provides novel heterocyclic amine derivatives having an excellent activity of inhibiting acyl-CoA:cholesterol acyltransferase, controlling, in mammals, absorption of cholesterol from the intestinal tract and suppressing accumulation of cholesterol ester at the arterial wall, thus being useful for the prophylaxis and therapy of hypercholesterolemia, atherosclerosis and various diseases caused by them (e.g. ischemic heart diseases such as cardiac infarction and cerebral blood vessel disorders such as cerebral infarction, apoplexy, etc.). The present invention further provides an industrially advantageous method of producing these novel compounds and also compositions or agents useful as medicines containing these novel compounds.

SUMMARY OF THE INVENTION

The present inventors conducted various studies on heterocyclic amine derivatives, and found that heterocyclic amine derivatives represented by the general formula (I),

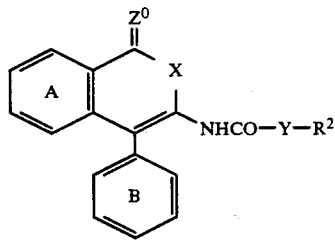
(I)

wherein a ring A and a ring B stand independently for an optionally substituted benzene ring, $Z^0$ stands for O or S or

stands for —CH$_2$—, X stands for O, S or NR$^1$ wherein R$^1$ stands for hydrogen atom or an alkyl group, Y stands for NH, O or (CH$_2$)n wherein n denotes 0 to 2, and R$^2$ stands for an optionally substituted hydrocarbon group, or their salts show strong action of inhibiting ACAT and are useful as a safe agent for lowering cholesterol in blood and a therapeutic drug of arteriosclerosis, and, based on this finding, the present invention was accomplished. More specifically, the present invention relates to (1) heterocyclic amine derivatives (I) or their salts, (2) a method of producing a heterocyclic amine derivative of the general formula (I'):

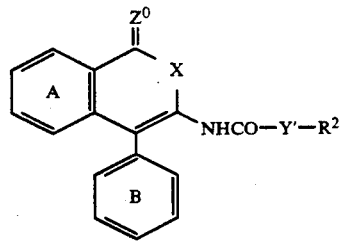
(I')

wherein Y' stands for NH or O and the other symbols are of the same meaning as defined above, or a salt thereof, which comprises reacting a compound of the general formula (II):

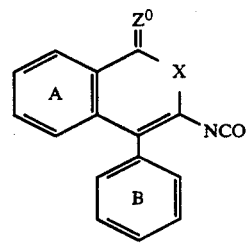
(II)

wherein the symbols are of the same meaning as defined above, or a salt thereof with a compound of the general formula (III):

R$^2$-Y'-H  (III)

wherein Y' and R$^2$ are of the same meaning as defined above, or a salt thereof, (3) a method of producing a heterocyclic amine derivative (I) or a salt thereof, which comprises reacting a compound of the general formula (IV):

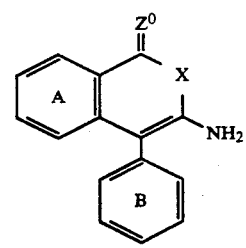
(IV)

wherein the symbols are of the same meaning as defined above, or a salt thereof with a compound of the general formula (V):

R$^2$-Y-CO$_2$H  (V)

wherein the symbols are of the same meaning as defined above, or a salt thereof or a reactive derivative thereof, and (4) an acyl CoA:cholesterol transferase inhibitor, which comprises a heterocyclic amine derivative (I) or a pharmaceutically acceptable salt thereof.

DETAILED DESCRIPTION OF THE INVENTION

In this specification, a ring A and a ring B stand independently for an optionally substituted benzene ring. Examples of substituents include, among others, halogen atoms (fluorine, chlorine, bromine and iodine), optionally halogenated alkyl groups, optionally halogenated alkoxy groups, optionally halogenated alkylthio groups, $C_{1-7}$ acylamino groups (e.g. formylamino, acetylamino, propionylamino, butylylamino, benzoylamino group, etc.), $C_{1-3}$ acyloxy groups (e.g. formyloxy, acetoxy, propionyloxy group, etc.) and hydroxyl group. Examples of halogen as the above-mentioned substituents include fluorine, chlorine, bromine and iodine, and preferable examples thereof are fluorine or chlorine.

As the optionally halogenated alkyl groups, use is made of, for example, $C_{1-6}$ straight-chain or branched alkyl groups or those substituted with one to five of such halogen as mentioned above. Among them, specific examples, which are often used, include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl, 5-trifluoromethylpentyl, etc., and preferable examples thereof are $C_{1-4}$ straight-chain or branched alkyl groups or those substituted with 1 to 3 halogen atoms such as methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, etc.

As the optionally halogenated alkoxy groups and the optionally halogenated alkylthio groups, use is made of, for example, those formed by bonding of the above-mentioned alkyl groups or halogenated alkyl groups with an oxygen atom or sulfur atom, respectively.

As the optionally halogenated alkoxyl groups, use is made of, for example, $C_{1-6}$ straight-chain or branched alkoxyl groups or those substituted with one to five of such halogen as mentioned above.

Among them, specific examples which are often used, include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy, etc., and preferable examples thereof are $C_{1-4}$ straight-chain or branched alkoxyl groups or those substituted with one to three halogen atoms such as methoxy, difluoromethoxy, trifluoromethoxy, ethoxy, 2,2,2-trifluoroethoxy, propoxy, isopropoxy, butoxy, isobutoxy, sec-butoxy, etc.

As the optionally halogenated alkylthio groups, use is made of, for example, $C_{1-6}$ straight-chain or branched alkylthio groups or those substituted with one to five of such halogen as mentioned above.

Among them, specific examples, which are often used, include methylthio, difluoromethylthio, trifluoromethylthio, ethylthio, propylthio, isopropylthio, butylthio, 4,4,4-trifluorobutylthio, pentylthio, hexylthio, etc., and preferable examples thereof are $C_{1-4}$ straight-chain or branched alkylthio groups or those substituted with one to three halogen atoms such as such methylthio, difluoromethylthio, trifluoromethylthio, ethylthio, propylthio, isopropylthio, butylthio, 4,4,4-trifluorobutylthio, etc.

Substituents on the ring A and the ring B may be at any position of these rings, and, when the number of the substituents is two or more, they may be the same one or different from one another, and the number may be in the range of 1 to 4. And, adjacent carbon atoms on the ring A or the ring B may form a 5- to 7-membered ring together with a group of the formula: $-(CH_2)l-$ wherein $l$ denotes an integer of 3 to 5, and such cases as above are also included in the object compounds (I).

Preferable examples of the ring A

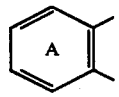

include an unsubstituted benzene ring

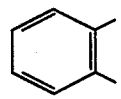

or substituted benzene ring e.g., a group of the formula:

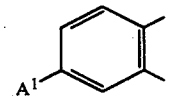

wherein $A^1$ is a halogen such as chlorine; a $C_{1-4}$ alkyl such as methyl, ethyl, isopropyl, etc.; a $C_{1-4}$ alkoxy such as methoxy; or a halogeno-$C_{1-4}$-alkyl such as trifluoromethyl, the formula:

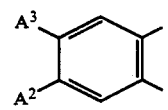

wherein $A^2$ and $A^3$ independently are a $C_{1-4}$ alkyl such as methyl or a $C_{1-4}$ alkoxy such as methoxy, or of the formula:

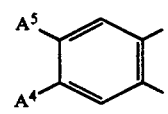

wherein $A^4$ and $A^5$ independently are a $C_{1-4}$ alkyl such as methyl. And preferable examples of the ring B

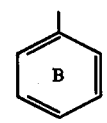

is an unsubstituted benzene ring or substituted benzene ring e.g., a group of the formula:

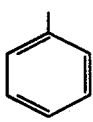

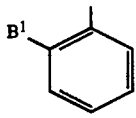

wherein $B^1$ is a halogen such as chlorine, fluorine, etc.; a $C_{1-4}$ alkyl such as methyl; or a $C_{1-4}$ alkoxy such as methoxy, the formula:

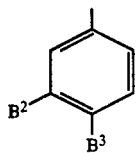

wherein $B^2$ and $B^3$ independently are a $C_{1-4}$ alkoxy such as methoxy, or the formula:

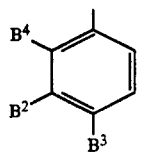

wherein $B^2$ and $B^3$ are as defined above and $B^4$ is a $C_{1-4}$ alkoxy such as methoxy.

X stands for O, S or $NR^1$. $R^1$ stands for hydrogen atom or an alkyl group.

As the alkyl group, straight-chain or branched $C_{1-6}$ alkyl, $C_{3-6}$ cycloalkyl or $C_{3-6}$ cycloalkyl-$C_{1-4}$ alkyl groups are preferable. The straight-chain or branched $C_{1-6}$ alkyl groups are exemplified by methyl, ethyl, propyl, isopropyl, butyl, isobutyl, sec-butyl, tert-butyl, pentyl, neopentyl and hexyl. Preferable examples of the straight-chain or branched $C_{1-6}$ alkyl groups include a straight-chain or branched $C_{1-4}$ alkyl group such as methyl, ethyl, propyl, isopropyl, butyl, isobutyl, sec-butyl, tert-butyl, pentyl, neopentyl and hexyl. The $C_{3-6}$ cycloalkyl groups are exemplified by cyclopropyl, cyclopentyl and cyclohexyl. And, the $C_{3-6}$ cycloalkyl-$C_{1-4}$ alkyl groups are exemplified by cyclopropylmethyl.

$R^2$ stands for an optionally substituted hydrocarbon group. As the hydrocarbon group shown by $R^2$, mention is made of, for example, alkyl, aryl and aralkyl group.

As the alkyl group shown by $R^2$, straight-chain or branched $C_{1-8}$ alkyl, $C_{3-8}$ cycloalkyl or $C_{3-8}$ cycloalkyl-$C_{1-4}$ alkyl groups are preferable. The straight-chain or branched $C_{1-6}$ alkyl groups are exemplified by methyl, ethyl, propyl, isopropyl, butyl, isobutyl, sec-butyl, tert-butyl, pentyl, isopentyl, neopentyl, hexyl, heptyl and octyl. Preferable examples of the straight-chain or branched $C_{1-6}$ alkyl groups include a straight-chain or branched $C_{1-4}$ alkyl group such as methyl, ethyl, propyl, isopropyl, butyl, isobutyl, sec-butyl, tert-butyl, pentyl, neopentyl and hexyl. The $C_{3-6}$ cycloalkyl groups are exemplified by cyclopropyl, cyclopentyl and cyclohexyl. And, the $C_{3-6}$ cycloalkyl-$C_{1-4}$ alkyl groups are exemplified by cyclopropylmethyl.

As the aryl group shown by $R^2$, $C_{6-10}$ aryl groups such as phenyl and naphthyl are preferable. More preferable examples of the $C_{6-10}$ aryl groups include $C_{6-8}$ aryl groups such as phenyl.

As the aralkyl group shown by $R^2$, $C_{7-16}$ aralkyl groups, for example, benzyl, 1-phenylethyl, 2-phenylethyl, 1-phenylpropyl, 2-phenylpropyl, 3-phenylpropyl and diphenylmethyl, are preferable. More preferable examples of the $C_{7-16}$ aralkyl groups include a $C_{7-13}$ aralkyl group, for example, benzyl, 1-phenylethyl, 2-phenylethyl, 1-phenylpropyl, 2-phenylpropyl, 3-phenylpropyl and diphenylmethyl. Particularly preferable ones of the $C_{7-13}$ aralkyl groups, for example, are benzyl, 1-phenylethyl, 2-phenylethyl and the like. Further, these alkyl, aryl and aralkyl groups shown by $R^2$ may have 1 to 5 substituents, preferably 1 to 3 substituents which may be the same one or different from one another. As such substituents, those used in the cases of the above-mentioned ring A and ring B are preferably used, and, besides, the following ones are also used.

As the aryl group shown by $R^2$, a phenyl group, for example, is preferable. The phenyl group may have, as substituents, 1 to 5 of, for example, halogen atoms, alkyl groups, alkoxy groups and mono- or di-$C_{1-4}$-alkylamino groups (e.g. dimethylamino, methylamino, etc.) Among them, phenyl groups having 1 to 5 halogen atoms (e.g. fluorine, chlorine, bromine, iodine), especially chlorine or fluorine, are especially preferable. More specific examples, of the halogenophenyl group include 2,4-difluorophenyl group. As the alkyl group which the said phenyl group may have as substituents, use is preferably made of, for example $C_{1-4}$ alkyl group such as methyl, ethyl or isopropyl. Especially, 2,6-dimethylphenyl, 2,6-diethylphenyl, 2-methyl-6-isopropylphenyl, 2.6-diisopropyl, etc. are preferable as a phenyl substituted by an alkyl group. As the alkoxy group which the said phenyl group may have, use is preferably made of, for example, a $C_{1-4}$ alkoxy group such as methoxy or ethoxy. Further, as $R^2$, are preferable phenyl groups having the above-mentioned $C_{1-4}$ alkyl groups, $C_{1-4}$ alkoxy groups and hydroxyl group or $C_{1-3}$ acyloxy group (e.g. formyloxy, acetoxy, etc.), as exemplified by 4-acetoxy-3,5-dimethylphenyl, 4-hydroxy-3,5-dimethylphenyl, 4-acetoxy-3,5-dimethoxyphenyl or 4-hydroxy-3,5-dimethoxyphenyl group. Particularly preferable examples of $R^2$ include, for example, 2,4-difluorophenyl, 2,6-difluorophenyl, 2,4,6-trifluorophenyl, 2,6-dimethylphenyl, 2,6-diisopropylphenyl, 4-acetoxy-3,5-dimethylphenyl, 3,5-diisopropyl-4-bydroxyphenyl, 3,5-dimethyl-4-hydroxyphenyl, 4-acetoxy-3,5-diisopropylphenyl, 3,5-diisopropyl-4-hydroxyphenyl, 3,5-di-t-butyl-4-hydroxyphenyl, 4-N,N-dimethylaminophenyl or cyclohexyl, and the like.

The heterocyclic amine derivatives of the formula (I) or their salts can be produced by, for example, the following methods 1 and 2. More specifically, 1 a heterocyclic isocyanate of the general formula (II) or a salt thereof is allowed to react with an amine or alcohol compound represented by the general formula (III) or a salt thereof to give a compound (I') (the compound (I) wherein Y is NH, or O) or a salt thereof, or 2 a heterocyclic amine of the general formula (IV) or a salt thereof is allowed to react with a substituted carboxylic acid of the general formula (V) or a salt thereof or a reactive derivative at the carboxyl group to give a compound (I) or a salt thereof.

The methods 1 and 2 will be described in detail as follows.

Method 1: In the case of allowing a compound (II) or a salt thereof to react with a compound (III) or a salt thereof (salts of compound (II) or (III) include those with a mineral acid such as hydrochloric acid or sulfuric acid, and those with an organic acid such as methanesulfonic acid, benzene sulfonic acid, toluene sulfonic acid, oxalic acid, fumaric acid, or maleic acid), the compound (III) itself can be used as the solvent, and the reaction can be conducted in any other solvent. As the solvent, any one can be employed unless it hampers the reaction, preferably exemplified by ethers (e.g. diethyl ether, diisopropyl ether, tetrahydrofuran, dioxane, dimethoxyethane, etc.), aromatic hydrocarbons (e.g. benzene, toluene, xylene, etc.), esters (e.g. methyl acetate, ethyl acetate, etc.), amides (e.g. N,N-dimethylformamide, etc.) and sulfoxides (e.g. dimethyl sulfoxide, etc.). In the case of using the compound (III) in the form of a salt, the reaction can be allowed to proceed advantageously by adding, upon necessity, a desalting agent. As the desalting agent, use is preferably made of, for example, tertiary amines such as trimethylamine, triethylamine or N-methylmorpholine, and aromatic amines such as pyridine, picoline or N,N-dimethylaniline. The amount of these desalting agent to be used ranges from 1 to 5 molar equivalents, preferably 1 to 3 molar equivalents relative to 1 mol. of the salt of (III). The reaction temperature ranges, usually, from $-10°$ C. to $180°$ C., preferably $0°$ C. to $120°$ C. The reaction time ranges usually from 15 minutes to 40 hours, preferably 30 minutes to 20 hours. The amount of (III) or its salt to be used ranges from 1 to 5 molar equivalents, preferably 1 to 3 molar equivalents relative to 1 mol. of (II) or a salt thereof.

Method 2: The reaction between a substituted carboxylic acid of the general formula (V) or a salt thereof or a reactive derivative thereof and (IV) or a salt thereof is to form an amide linkage, which is conducted by various methods. For example, in the case of allowing a compound (IV) or a salt thereof (e.g. salts with mineral acid such as hydrochloric acid or sulfuric acid, or salts with organic acid such as methanesulfonic acid, benzene sulfonic acid, toluenesulfonic acid, oxalic acid, fumaric acid or maleic acid) to react with a compound (V) or a salt thereof (e.g. salts with alkali metal or alkaline earth metal such as sodium, potassium or magnesium), the reaction is preferably conducted usually by using a suitable condensing agent, or by once leading (V) or a salt thereof to its reactive derivative, then allowing it to react with (IV) or a salt thereof. As the condensing agent, use is made of, for example, dicyclohexylcarbodiimide (DCC), diethyl cyanophosphate (DEPC) and diphenyl phosphoryl azide (DPPA). In the case of using these condensing agents, the reaction is usually conducted in a solvent (e.g. ethers, esters, hydrocarbons, amides and sulfoxides, such as tetrahydrofuran, dioxane, dimethoxyethane, ethyl acetate, benzene, toluene, N,N-dimethylformamide, dimethyl sulfoxide, etc.). This reaction may be accelerated in the presence of a base. This reaction is conducted at temperatures ranging from about $-10°$ C. to $100°$ C., preferably about $0°$ C. to $60°$ C. The reaction time ranges usually from about 1 to 96 hours, preferably about 1 to 72 hours. Amounts of (V) or a salt thereof and the condensing agent are respectively 1 to 5 molar equivalents, preferably 1 to 3 molar equivalents relative to 1 mol. of (IV) or a salt thereof. As the base, use is made of, for example, alkyl amines such as triethylamine, or cyclic amines such as N-methyl morpholine or pyridine, and the amount of the base to be used ranges from 1 to 5 molar equivalents, preferably 1 to 3 molar equivalents relative to 1 mol. of (IV) or a salt thereof.

As the reactive derivative of (V), use is made of, for example, an acid halide (e.g. chloride, bromide, etc.), acid anhydride, mixed acid anhydride (e.g. anhydride with methyl carbonate, anhydride with ethyl carbonate, anhydride with isobutyl carbonate, etc.), active ester (e.g. ester with hydroxy succinic acid imide, ester with 1-hydroxybenzotriazole, ester with N-hydroxy-5-norbornene-2,3-dicarboxyimide, ester with p-nitrophenol, ester with 8-oxyquinoline, etc.), and especially acid halide is preferable. In the case of allowing a compound (IV) or a salt thereof to react with a reactive derivative of (V), the reaction is usually conducted in a solvent (e.g. halogenated hydrocarbons, ethers, esters, hydrocarbons and amides, such as chloroform, dichloromethane, ethyl ether, tetrahydrofuran, dioxane, dimethoxyethane, ethyl acetate, benzene, toluene, pyridine or N,N-dimethylformamide). The reaction may be accelerated in the presence of a base, and it is usually conducted at temperatures ranging from about $-10°$ C. to $120°$ C., preferably about $0°$ C. to $100°$ C. The reaction time usually ranges from about 1 to 48 hours, preferably about 1 to 24 hours. The amount of the reactive derivative of (V) to be used ranges from 1 to 5 molar equivalents, preferably 1 to 3 molar equivalents, relative to 1 mol. of (IV) or a salt thereof. As the base, use is made of, for example, alkyl amines such as triethylamine, cyclic amines such as N-methyl morpholine or pyridine, aromatic amines such as N,N-dimethyl aniline or N,N-diethyl aniline, carbonates of alkali metal such as sodium carbonate or potassium carbonate, or hydrogencarbonates of alkali metal such as sodium hydrogencarbonate or potassium hydrogencarbonate. The amount of the base to be used ranges from 1 to 5 molar equivalents, preferably 1 to 3 molar equivalents, relative to 1 mol. of (IV) or a salt thereof. And, in the case of using a solvent immiscible with water, the reaction may be allowed to proceed in two phases by adding water to the reaction system.

In the above-mentioned method 2, when the compound (V) wherein Y stands for O is used, preferable reactive derivatives of (V) include acid halides and active esters. And, when the compound (V) wherein Y stands for NH, preferable reactive derivatives of (V) include isocyanate compounds of the formula:

$$R^2-N=C=O \qquad (VI)$$

wherein the symbol is of the same meaning as defined above. In the case of using this compound (VI) and the compound (IV) or a salt thereof, the object compound (I) (Y=NH) can be obtained by allowing the compound (VI) to react with the compound (IV) or a salt thereof under conditions similar to those in the above-mentioned method 1. In this reaction, in the case of using (IV) as the form of salt, a desalting agent similar to that used in the method 1 can be used. The amount of the compound (VI) usually ranges from 1 to 5 molar equivalents, preferably from 1 to 3 molar equivalents, relative to 1 mol. of (IV) or a salt thereof.

When the compound (I) or a salt thereof produced by the above-mentioned method 1 or 2 contains lower alkoxy groups on the ring A, ring B and benzene ring of $R^2$, they can be changed, when necessary, into hydroxyl groups by allowing them to react with, for example, boron tribromide. This reaction is conducted usually in a solvent (e.g. halogenated hydrocarbons or hydrocarbons such as dichloromethane, chloroform, carbon tetrachloride, benzene or toluene) at temperatures ranging from about $-20°$ C. to $80°$ C., preferably about $0°$ C. to $30°$ C., and the amount of boron tribromide to be used ranges from about 1 to 10 molar equivalents, preferably about 1 to 5 molar equivalents relative to one lower alkoxy group. The reaction time ranges usually from about 15 minutes to 24 hours, preferably about 30 minutes to 12 hours.

When the compound (I) or a salt thereof produced by the above-mentioned method 1 or 2 contains hydroxyl groups on the ring A, ring B and benzene ring of $R^2$, they can be changed, when necessary, into an alkoxy or acyloxy group by subjecting the hydroxyl groups to alkylation or acylation. The alkylation is conducted by using an alkylating agent, for example, halide of an optionally substituted alkane (e.g. chloride, bromide, iodide, etc.), sulfuric acid ester or sulfonic acid ester (e.g. methanesulfonate, p-toluene sulfonate, benzenesulfonate, etc.) in a solvent (for example, alcohols such as methanol, ethanol, propanol, etc., ethers such as dimethoxyethane, dioxane, tetrahydrofuran, etc., ketones such as acetone, etc., amides such as N,N-dimethylformamide, etc.) in the presence of a base (for example, an organic base such as trimethylamine, triethylamine, N-methyl morpholine, pyridine, picoline, N,N-dimethyl aniline, etc., an inorganic base such as potassium carbonate, sodium carbonate, potassium hydroxide, sodium hydroxide, etc.). The reaction temperature usually ranges from about $-10°$ C. to $100°$ C., preferably about $0°$ C. to $80°$ C. The amount of these alkylating agents to be used ranges from about 1 to 5 molar equivalents, preferably from about 1 to 3 molar equivalents relative to 1 mol. of the phenolic derivative employed as a material. The reaction time usually ranges from about 15 minutes to 24 hours, preferably about 30 minutes to 12 hours.

The acylation is conducted by reacting the phenolic derivative with a desired carboxylic acid or its reactive derivative to be used as an acylating agent. This reaction is conducted, varying with kinds of acylating agents and kinds of phenolic derivatives employed as a material, usually in a solvent (e.g. hydrocarbons, ethers, esters, halogenated hydrocarbons, amides, aromatic amines such as benzene, toluene, ethylether, ethyl acetate, chloroform, dichloromethane, dioxane, tetrahydrofuran, N,N-dimethylformamide, pyridine, etc.), and for accelerating the reaction, a suitable base (e.g. hydrogen carbonate such as sodium hydrogencarbonate, potassium hydrogencarbonate, etc., carbonate such as sodium carbonate, potassium carbonate, etc., acetate such as sodium acetate, etc., tertiary amines such as triethylamine, aromatic amines such as pyridine, etc.) can be added to the reaction system. As the reactive derivatives of carboxylic acid, use is made of an acid anhydride, mixed acid anhydride, acid halide (e.g. chloride, bromide), among others. The amount of these acylating agents to be used ranges from 1 to 5 molar equivalents, preferably 1 to 3 molar equivalents relative to 1 mol. of the phenolic derivative employed as a material. The reaction temperature ranges usually from about $0°$ C. to $150°$ C., preferably about $10°$ C. to $100°$ C. The reaction time ranges usually from about 15 minutes to 12 hours, preferably about 30 minutes to 6 hours.

When a compound (I) is obtained in the free form by the above-described method, it can be led, by a conventional method, to the salt with, for example, a mineral acid (e.g. hydrochloric acid, sulfuric acid and hydrobromic acid) or an organic acid (e.g. methanesulfonic acid, benzenesulfonic acid, toluenesulfonic acid, oxalic acid, fumaric acid, maleic acid and tartaric acid), and, when a compound (I) is obtained in the form of salt, it can be led, by a conventional method, to the free form or any other salt.

The object compound (I) or a salt thereof can be purified and recovered by a per se known separating and purifying means (e.g. concentration, solvent extraction, column chromatography and recrystallization).

The compound (I) or its pharmaceutically acceptable salts have an excellent action of inhibiting acyl-CoA:-cholesterol acyltransferase (ACAT), and their acute toxicity and toxicity observed in their continuous administration are both weak, thus being safe as medicines. ACAT is an enzyme causing higher fatty acid esterification of intracellular cholesterol, and it has been known that ACAT plays an important role in accumulation of cholesterol ester in the small intestine. Therefore, ACAT-inhibiting substances inhibit the absorption of alimentary cholesterol from intestinal tract, suppress the increase of value of cholesterol in blood, suppress the accumulation of intracellular cholesterol ester in the lesion of arteriosclerosis and can prevent the development of atherosis. The compound (I) of this invention having an excellent ACAT-inhibiting activity and its salts are, therefore, are useful as safe prophylactic and therapeutic agents for hypercholesterolemia, atherosclerosis and various diseases caused by them (e.g. ischemic heart diseases such as cardiac infarction and cerebral blood vessel disorders such as cerebral infarction, apoplexy, etc.) in mammals (e.g. mouse, rat, hamster, rabbit, cat, dog, horse, cow, sheep, monkey and man).

And, the compound (I) and its salts include those showing an action to suppress the formation of lipid peroxide (anti-oxidizing action). It has been known that peroxidation of lipid in a living body is closely related to causes of arteriosclerosis or ischemic diseases in brain and cardiovascular system. Therefore, the compound (I) and its salts having both ACAT-inhibiting activity and anti-oxidizing activity can be used for prophylaxis and therapy of various diseases caused by cholesterol in blood and lipid peroxide, and they are remarkably useful as medicines.

In the case of using a compound of the general formula (I) or a pharmaceutically acceptable salt thereof is used as the above-mentioned medicines, they may be mixed with a suitable pharmacologically acceptable carrier, excipient or diluent, and can be administered orally or non-orally in the form of powder, granule, tablet, capsule or injection, and, when they are used for inhibiting the absorption of cholesterol, oral administration is preferable. While the dosage varies with types of the compound (I) or salts thereof, administration route, symptoms, ages of patients, etc., it is, when, for example, administered orally to an adult patient of hypercholesterolemia, about 0.005 to 50 mg, preferably about 0.05 to 10 mg, more preferably about 0.2 to 4 mg /kg(body weight)/day once to three times a day.

The compound (II) or its salts or (IV) or its salts employed for producing the compound (I) of this invention or its salts are novel compounds, and they can be produced, with industrial advantage, by, for example, the method shown by the following reaction schema or methods analogous thereto.

compound. For this reaction, various reports have been made on literature references, and any one of them can be applied to (VIII).

For example, by allowing an azidation agent (e.g. diphenyl phosphoryl azide (DPPA)) to react with (VIII), the acid azide compound of (VIII) can be pro-

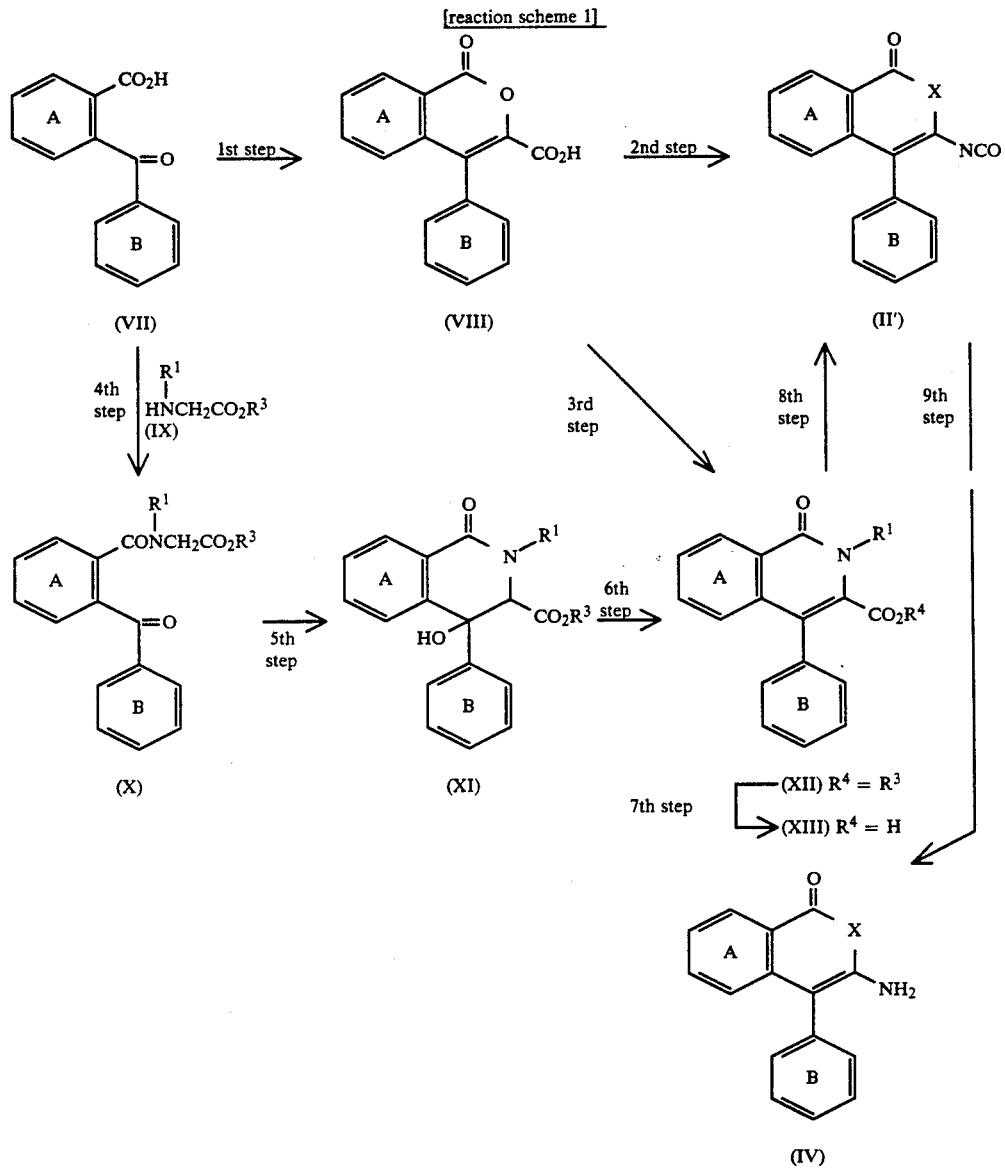

[reaction scheme 1]

wherein a ring A, a ring B, $R^1$ and X are of the same meaning as defined above, $R^3$ stands for a protecting group of a carboxyl group and $R^4$ stands for hydrogen atom or a protecting group of a carboxyl group.

In the foregoing reaction schema, a 2-benzoyl benzoic acid derivative represented by the formula (VII) is employed as the starting material.

The first step is to obtain 4-phenylisocoumarin-3-carboxylic acid (VIII), and it is conducted by, for example, a known method [e.g. F. Duro P. Condorelli, Boll. Accad. Gioenia Sci. Nat. Catania, Vol. 5, p 606, 1960] or a method analogous thereto.

The second step is to obtain (II') (X=-O-) by changing the carboxyl group of (VIII) into an isocyanate group, and it usually comprises changing of (VIII) through its acid azide compound into an isocyanate duced. This reaction can be conducted usually in a solvent inert to the reaction (e.g. ethers such as ethyl ether, isopropyl ether, dimethoxyethane, tetrahydrofuran or dioxane, aromatic hydrocarbons such as benzene, toluene or xylene, esters such as methyl acetate or ethyl acetate, ketones such as acetone or 2-butanone, aromatic amines such as pyridine, amides such as N,N-dimethylformamide). The reaction can also be allowed to proceed in the presence of a base (e.g. trimethylamine, triethylamine or N-methyl morpholine). The reaction time ranges usually from about 5 minutes to 12 hours, preferably about 10 minutes to 6 hours. The reaction temperature ranges usually from about −10° C. to 150° C., preferably about −5° C. to 120° C. The amount of DPPA to be used ranges from 1 to 3 molar equivalents, preferably 1 to 2 molar equivalents relative to 1 mol. of (VIII).

While the acid azide thus produced can be isolated and purified by a per se known means, usually the reaction mixture itself is heated, without isolating the acid azide, to change into the isocyanate compound (II'). This reaction is conducted preferably in a solvent similar to that used for azidation at temperatures usually ranging from about 20° C. to 200° C., preferably about 30° C. to 150° C. The reaction time ranges usually from about 5 minutes to 10 hours, preferably about 5 minutes to 6 hours. Thus obtained compound (II') can be used as the material for producing the compound (I) or (IV) after isolating by a per se known means or without isolation.

The third step is to convert isocoumarin carboxylic acid (VIII) to isoquinolone carboxylic acid (XIII), and it is conducted by, for example, a known method [e.g. N. A. Santagati, E. Bousquet, G. Romeo, A. Caruso and A. Prato, Bolletino Chimico Farmaceutico, Vol. 125, p 437, 1986] or a method analogous thereto. Isoquinolone carboxylic acid (XIII) is produced also by starting from (VII) through the 4th to 7th steps.

The 4th step is to obtain the amide compound (X) by allowing the carboxyl group of (VII) to react with the amino group of the glycine derivative (IX). In this reaction, the reaction between (VII) or a reactive derivative at its carboxyl group and (IX) can be conducted under conditions similar to those of the reaction in the production of (I) by the reaction of the above-mentioned (IV) and (V) (Method 1).

The 5th step is to process the compound (X) with a base for causing intramolecular addition reaction to obtain the ring-closed compound (XI). As the base to be employed for this reaction, for example, use is preferably made of an organic base such as 1,5-diazabicyclo[4.3.0]non-5-ene (DBN), 1,8-diazabicyclo[5.4.0]undec-7-ene (DBU) or N-benzyltrimethylammonium hydroxide (Triton B), and an inorganic base such as sodium methoxide, sodium ethoxide, sodium hydride, potassium hydride, n-butyl lithium or lithium diisopropylamide, and besides such bases as employed in the reaction of (IV) with (V) (Method 1) can also be used. The amount of the base ranges usually from 0.5 to 20 molar equivalents, preferably 1 to 5 molar equivalents, relative to 1 mol. of (X). This reaction is conducted usually in a solvent. As the solvent, use is made of such one as employed in the reaction of (IV) with (V) (Method 1), The reaction temperatures varies with the kinds of the base then employed, and it ranges usually from about −80° C. to 200° C., preferably about −50° C. to 150° C. The reaction time varies with the starting materials, bases, reaction temperatures and kinds of solvent then employed, and it ranges usually form about 10 minutes to 24 hours.

The 6th step is to produce the isoquinolone derivative (XII) by subjecting the compound (XI) to dehydration reaction.

This reaction is preferably conducted usually in the presence of an acid catalyst. As the acid catalyst, use is made of, for example, a sulfonic acid compound such as p-toluenesulfonic acid or methanesulfonic acid, a carboxylic acid compound such as acetic acid or trifluoroacetic acid, an inorganic acid compound such as hydrogen chloride, hydrogen bromide or sulfuric acid, and a Lewis acid compound such as boron ethyl ether trifluoride or aluminum chloride. The amount of the acid catalyst to be employed ranges from 0.1 to 20 molar equivalents, preferably 0.1 to 5 molar equivalents relative to 1 mol. of (XI). As the solvent, use may be made of such ones as employed in the reaction between (IV) and (V) (Method 1). While the reaction temperatures vary with kinds of the acid then employed, it usually ranges from about −10° C. to 200° C., preferably 0° C. to 150° C. While the reaction time varies with the starting materials, bases, reaction temperatures and kinds of the solvent, it ranges usually from about 30 minutes to 24 hours.

In the 5th step, there are cases in which a dehydrated-cyclized compound can be obtained as a product depending on the type of compound (X), the base employed, kind of the solvent, reaction temperature or reaction time.

The 7th step is to obtain the compound (XIII) by removing the protecting group $R^4$ of the carboxyl group of (XII). This reaction is conducted by, depending on kinds of $R^4$ of (XII), various known methods [e.g. T. W. Greene, Protective Groups in Organic Synthesis, John Wiley & Sons, New York, 1981, p 157-187]. For example, when the protective group of (XII) is a lower alkyl group such as methyl or ethyl, the reaction is conducted under conditions analogous to those of hydrolysis as described, for example, in the following 9th step.

The 8th step is to convert the isoquinolone carboxylic acid (XIII) into the isocyanate compound (II'). This step can be conducted in accordance with the process described in the second step.

The 9th step is to obtain (IV) by converting the isocyanate group of (II') to an amino group. This step is usually conducted under hydrolytic conditions. This reaction is conducted, for example, in a solvent (e.g. alcohols such as methanol, ethanol, propanol or butanol, ethers such as tetrahydrofuran, dioxane or dimethoxyethane, or a mixture solvent of them), under alkaline conditions using hydroxide of alkali or alkaline earth metal such as sodium hydroxide or barium hydroxide, or acid conditions using an inorganic acid such as hydrochloric acid, hydrobromic acid or sulfuric acid. The reaction temperature ranges usually from about 0° C. to 120° C., preferably from about 15° C. to 100° C. The reaction time ranges from about 30 minutes to 36 hours, preferably from about one hour to 20 hours. And, (IV) can also be obtained by subjecting (I') wherein Y' is O, to hydrolysis as described above.

The starting compound (VIII) in the above schema can also be produced by, for example, a known method [e.g. P. Aeberli, P. Eden, J. H. Gogerty, W. J. Houlihan, and C. Penberthy, J, Med. Chem., 18, 177(1975)] or methods analogous thereto In the above reaction schema 1, the compounds (II) and (IV) wherein $Z^o$ stands for O and X stands for O or $NR^1$ are described, but the compounds (II) and (IV) wherein $Z^o$ stands for O and X stands for S and the compounds (II) and (IV) wherein $Z^o$ stands for S and X stands for O, S or $NR^1$ can be produced by a similar method as mentioned above in the 1st step to 9th step or a method analogous thereto The starting material (II) or (IV) for producing the compound (I) wherein

stands for —CH$_2$— and X stands for S or a salt thereof are novel compounds, and they can be produced, with industrial advantage, by, for example, the method shown by the following reaction schema 2 or methods analogous thereto.

[reaction scheme 2]

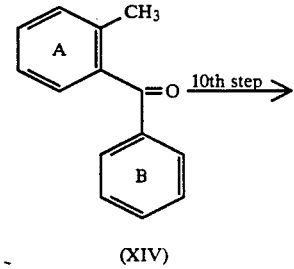

(XIV)

10th step →

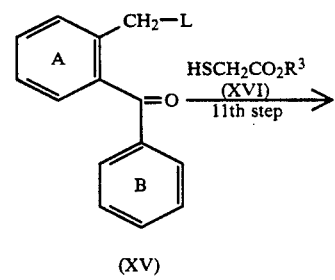

(XV)

$\xrightarrow{\text{HSCH}_2\text{CO}_2\text{R}^3}_{\substack{\text{(XVI)} \\ \text{11th step}}}$

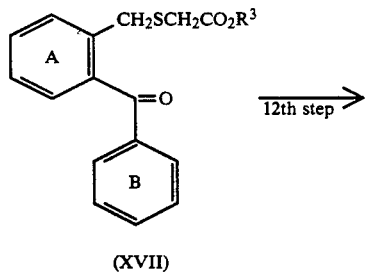

(XVII)

12th step →

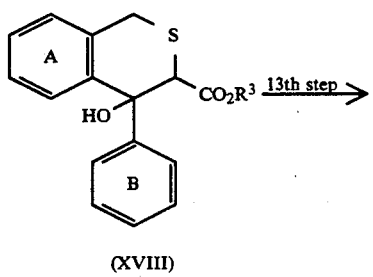

(XVIII)

13th step →

-continued
[reaction scheme 2]

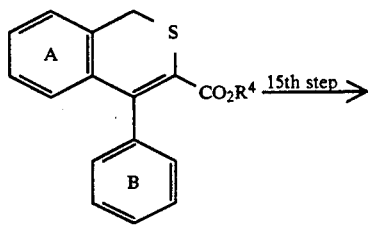

15th step →

14th step $\begin{bmatrix} \text{(XIX) R}^4 = \text{R}^3 \\ \text{(XX) R}^4 = \text{H} \end{bmatrix}$

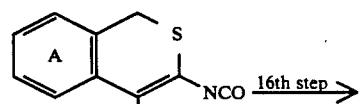

16th step →

(II')

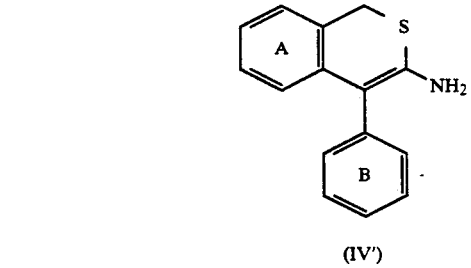

(IV')

wherein the ring A, the ring B, R$^3$ and R$^4$ are of the same meaning as defined above, and L stands for halogen atom.

In the reaction schema 2, a 2-methylbenzophenone derivative represented by the formula (XIV) is employed as the starting material The 10th step is to obtain 2-halogenomethylbenzophenone (XV), and it is conducted by, for example, a known method [e.g. R. Faragher and T. L. Gilichrist, J. Chem. Soc., Perkin I, 1976, p336] or a method analogous thereto.

The 11th step is to obtain (XVII) by reacting the removable halogen atom of (XV) with a thiol group of (XVI). In this step a thioglycolic acid ester represented by (XVI) is used as thiol compound.

The compound (XVI) can be used in a free form or in a form of salt, for example, a salt with an alkaline metal such as lithium, sodium or potassium or a salt with an alkaline earth metal such as calcium or magnesium. The amount of the compound (XVI) or its salt to be reacted ranges from 1 to 10 mol., preferably to 5 mol. relative to 1 mol. of the compound (XV). This reaction can be conducted usually in a solvent. The solvent preferably includes, for example, halogenated hydrocarbons such as dichloromethane or chloroform, nitriles such as acetonitrile, ethers such as dimethoxyethane or tetrahydrofurane, dimethylformamide, dimethyl sulfoxide or hexamethylphosphoroamide. The reaction proceeds advantageously by adding a base. The base includes, for example, sodium hydrogencarbonate, potassium hydrogencarbonate, sodium carbonate, potassium carbonate, sodium hydride, potassium hydride, sodium amide, sodium methoxide, triethylamine, diisopropylethylamine, pyridine, etc. In this reaction, the compound (XVI) can be reacted, after being changed into an alkaline matal salt or alkaline earth metal salt as mentioned above, instead of using such base, with the compound (XV). The amount of the base then employed varies with kinds of the compound (XV) and (XVI) then employed, kinds of the solvent, other reaction condition, and it ranges usually from 1 to 10 mol., preferably from 1 to 5 mol., relative to 1 mol. of compound (XV). The reaction temperature ranges from about $-50°$ C. to $100°$ C., preferably about $-30°$ C. to $80°$ C. The raction time varies with kinds of the compound (XV), kinds of the compound (XVI) or its salt or the reaction temperature, and it ranges from 1 to 72 hours, preferably from 1 to 24 hours.

From the compound (XVII) to (XVIII) (the 12th step), from (XVIII) to (XIX) (the 13th step) and from (XIX) to (XX) (the 14th step) can be conducted by a similar method as (X)→(XI) (the 5th step), (XI)→(XII) (the 6th step), and (XII)→(XIII) (the 7th step), respectively as described above in the reaction schema 1 or methods analogous thereto. In the 12th step, there is a case where dehydrated-cyclized compounds (XIX) are obtained as product depending on the type of (XVII), the base employed, kinds of the solvent, the reaction temperature or the raction time. From the compound (XX) to (II') (the 15th step) and from (II') to (IV'') (the 16th step) can be conducted by a similar method as (VIII)→(II') (the 2nd step) and (II')→(IV') (the 9th step), respectively as described above in the reaction schema 1 or methods analogous thereto.

In the above reaction schema 2, the compounds (II) or (IV) wherein

stands for —CH$_2$— and X stands for S are described, but the compounds (II) or (IV) wherein

stands for —CH$_2$— and X stands for O or NR$^1$ can be produced by a similar method as mentioned above in the 10th step to 16th step or methods analogous thereto.

Each of the compounds obtained in each of the above-described first to 16th steps may be purified and recovered by a per se known purification means, for example, concentration, pH-change, phase transfer, solvent-extraction, column chromatography, crystallization or recrystallization, or may be used, in the state of a mixture without isolation, for the subsequent reaction steps.

The compound (I) or its salts of this invention have an excellent ACAT-inhibiting activity, and results of the pharmacological test are shown as follows.

(1) Acyl-CoA:cholesterol transferase (ACAT)-inhibiting action

[Method of Experiment]

The enzyme specimen ACAT was prepared from the microsomal fraction of mucosal cells from the small intestines of 6-week old Sprague-Dawley rats fasted for 20 hours, in accordance with the method described by Heider, et al. on Journal of Lipid Research, Vol. 24, p. 1127 (1982).

The activity of ACAT was calculated by determining the amount of labeled cholesterol ester formed from [1-$^{14}$C]oleyl-CoA and endogenous cholesterol.

[Results]

In Table 1, the inhibition rate (%) of formation of labeled cholesterol ester by the addition of test compounds (representing the compounds obtained by the following Working Examples 1 to 31) in an amount of $10^{-6}$M is shown as the index of the action of inhibiting ACAT.

TABLE 1

| Test Compound (Example No.) | ACAT inhibiting rate (%) $10^{-6}$M |
|---|---|
| 1 | 98.0 |
| 2 | 76.1 |
| 8 | 64.9 |
| 9 | 89.8 |
| 10 | 98.5 |
| 11 | 92.1 |
| 12 | 94.2 |
| 13 | 95.8 |
| 14 | 99.0 |
| 15 | 99.4 |
| 16 | 60.2 |
| 17 | 65.7 |
| 18 | 83.2 |
| 19 | 97.7 |
| 20 | 88.7 |
| 23 | 54.3 |
| 26 | 94.8 |
| 27 | 99.3 |
| 28 | 92.0 |
| 29 | 95.5 |

Table 1 shows that the compound (I) or its salts have an excellent ACAT-inhibiting activity.

(2) Plasma cholesterol lowering activity in cholesterol fed rat

[Method of Experiment]

7-week old, male Sprague-Dawley rats were fed a 1% cholesterol diet (containing 0.5% cholic acid and 5% olive oil) for three days, and then the rats were grouped according to the plasma cholesterol level (n=5). They were fed with the diet as described above containing test compound for further 4 days. Blood was collected from the rats during 8:30–10:00 am at the fed state, and the plasma cholesterol level was measured enzymatically. The amount of test compound consumed by rats was calculated on the basis of the amount of the diet consumed by the rats.

[Results]

Table 2 shows plasma cholesterol lowering activity by the test compound in the cholesterol fed rat

TABLE 2

| Test Compound (Example No.) | Dose (mg/kg/day) | Chloesterol in Serum (mg/dl) |
|---|---|---|
| Control | 0 | 191.0 ± 25.6 |
| 14 | 0.14 | 103.4 ± 23.7* |
| 15 | 0.13 | 125.2 ± 22.6* |

The values are mean values ± standard deviations.
*$p < 0.05$ (Duncan's multiple test vs. control group)

It is proved by the above Table 2 that the compound (I) and their salts possess excellent activity for lowering plasma cholesterol.

WORKING EXAMPLES

The present invention will be described in further detail by the following Reference Examples and Working Examples, but these Examples are mere examples and not intended to limit the scope of this invention, and they may be modified so long as the modification does not deviate from the scope of this invention. The following abbreviations used in the Examples and Reference Examples have the following meanings: mg: milligram, g:gram, ml: milliliter, mmol: millimole, ppm: parts per million, NMR: nuclear magnetic resonance, H: hertz, MHZ: megahertz, s: singlet, d: doublet, t: triplet, q: quartet, m: multiplet, J: coupling constant, M.p.: melting point.

Elution in the column chromatography in Reference Examples and Working Examples was carried out, unless otherwise specified, under observation by means of TLC (Thin Layer Chromatography). In the TLC observation, 60 $F_{254}$ manufactured by Merck in U. S. A. was employed as TLC plate, the solvent used as the eluent in the column chromatography was employed as developing solvent, and a UV detector was employed as the method of detection. As silica gel for column chromatography, silica gel 60 (70–230 mesh) manufactured by Merck in U. S. A. was employed. Room temperature means usually 10° C. to 35° C.

REFERENCE EXAMPLE 1

6-Chloro-4-phenylisocoumarin-3-carboxylic acid

A mixture of 2-benzoyl-4-chlorobenzoic acid (2.60 g), acetone (60 ml), dimethylformamide (3 ml), potassium carbonate (1.40 g) and diethyl bromomalonate (1.85 ml) was stirred for 16 hours at room temperature. The solvent was distilled off. To the residue was added ethyl acetate. The mixture was washed with water, and dried ($Na_2SO_4$), then the solvent was distilled off to leave an ester compound as a colorless oily substance. To this oily substance were added acetic acid (40 ml) and hydrochloric acid (40 ml). The mixture was heated for 3 hours at 110° C. The reaction mixture was concentrated, then there was added water, followed by extraction with ethyl acetate. The extract solution was washed with water and dried ($Na_2SO_4$), then the solvent was distilled off to afford the above-titled compound as colorless crystals (2.70 g).

M.p. 206°–208° C. (recrystallized from ethyl acetate-isopropyl ether)

Elemental Analysis for $C_{16}H_9O_4Cl$: Calcd.: C, 63.91; H, 3.02; Found : C, 63.80; H, 2.95

REFERENCE EXAMPLE 2

6-Chloro-4-phenyl-1(2H)-isoquinolinone-3-carboxylic acid

To a solution of the compound (0.50 g) obtained in Reference Example 1 in methanol (6 ml) was added 5N-$NH_3$/MeOH (8 ml). The mixture was stirred for 7 hours at room temperature. The solvent was distilled off. To the residue was added water. This mixture was made acid with 1N-HCl, followed by extraction with ethyl acetate. The extract solution was washed with water and dried ($Na_2SO_4$), then the solvent was distilled off to leave an amide compound as a colorless oily substance. To this oily substance was added 4N-HCl-ethyl acetate (6 ml), and the mixture was stirred for 16 hours at room temperature. The solvent was distilled off. To the residue were added water and acetone, and the mixture was stirred for 30 minutes. Precipitated crystals were collected by filtration and washed with water, acetone and ether, successively to afford the above-titled compound as colorless crystals (0.32 g).

M.p.>300° C. (recrystallized from acetone-methanol)

Elemental Analysis for $C_{16}H_{10}NO_3Cl$: Calcd.: C, 64.12; H, 3.36; N, 4.67; Found : C, 64.03; H, 3.38; N, 4.67

REFERENCE EXAMPLE 3

6-Chloro-2-methyl-4-phenyl-1(2H)-isoquinolinone-3-carboxylic acid

Starting from the compound (3.01 g) obtained in Reference Example 1, the reaction was allowed to proceed in a manner similar to that of Reference Example 2, using methylamine instead of ammonia in Reference Example 2, to afford the above-titled compound (3.40 g).

M.p. 248°–250° C.

REFERENCE EXAMPLE 4

4-(4-Fluorophenyl)-2-methyl-1(2H)-isoquinoline-3-carboxylic acid

Starting from 4-(4-fluorophenyl)isocoumarin-3-carboxylic acid (2.00 g), a reaction was allowed to proceed in a manner similar to that of Reference Example 2, using methylamine, to afford the above-titled compound (1.73 g).

M.p. 196°–197° C.

REFERENCE EXAMPLE 5

4-(2-Methylphenyl)-2,6,7-trimethyl-1(2H)-isoquinolinone-3-carboxylic acid

Step 1

N-[4,5-Dimethyl-2-(2-methylbenzoyl)benzoyl]-N-methyl glycine ethyl ester

A mixture of 4,5-dimethyl-2-(2-methylbenzoyl)benzoic acid (705 mg), 1-hydroxybenzotriazole (490 mg), 1,3-dicyclohexylcarbodiimide (660 mg) and tetrahydrofuran (20 ml) was stirred for one hour at room temperature. Precipitated crystals were filtered off. To the filtrate were added N-methyl glycine ethyl ester hydrochloride (600 mg) and triethylamine (0.55 ml). The mixture was stirred for 16 hours at room temperature. The solvent was distilled off. To the residue was added ethyl acetate. This mixture was washed with water, a 10% aqueous solution of potassium hydrogensulfate, a saturated aqueous solution of sodium hydrogencarbonate and water, successively, which was then dried ($MgSO_4$), followed by distilling off the solvent. The residue was subjected to a silica gel column chromatography (hexane - ethyl acetate=3:1→1:1) to give the above-titled compound as a yellow oily substance (880 mg).

IR$\nu_{max}^{Neat}$cm$^{-1}$: 1740, 1640, 1600, 1550, 1440, 1400, 1300

NMR(200 MHz, CDCl$_3$)ppm: 1.31(3H,t,J=7Hz), 2.23(1H,s), 2.25(2H,s), 2.28(1H,s), 2.34(2H,s), 2.39(3H,s), 2.95(2H,s), 3.04(1H,s), 3.96(0.67H,s), 4.19(1.33H,s), 4.23(2H,q,J=7Hz), 7.14–7.46(5H,m)

Step 2

Ethyl ester of 4-(2-methylphenyl)-2,6,7-trimethyl-1(2H)-isoquinolinone-3-carboxylic acid To a solution of the compound (858 mg) obtained in Step 1 in toluene (15 ml) was added 1,8-diazabicyclo[5.4.0]undec-7-ene (0.5 ml). The mixture was refluxed for 9 hours. The solvent was distilled off. To the residue was added ethyl acetate, which was washed with water, a 10% aqueous solution of potassium hydrogensulfate and water, successively, then dried (MgSO$_4$), followed by distilling off the solvent. The residue was subjected to a silica gel column chromatography (hexane - ethyl acetate=3:1→1:1) to give the above-titled compound as colorless crystals.

M.p. 126°–128° C. (recrystallized from ethyl ether - isopropyl ether)

IR$\nu_{max}^{Nujol}$cm$^{-1}$: 1720, 1645, 1610, 1595, 1490

NMR(200MHz,CDCl$_3$)ppm : 0.89(3H,t,J=7Hz), 2.09(3H,s), 2.25(3H,s), 2.40(3H,s), 3.61(3H,s), 3.98(2H,q,J=7Hz), 6.73(1H,s), 7.11–7.39(4H,m), 8.27(1H,s)

Step 3

4-(2-Methylphenyl)-2,6,7-trimethyl-1(2H)-isoquinolinone-3-carboxylic acid

A mixture of the compound (87 mg) obtained in Step 2, 1N-NaOH (1.5 ml) and ethanol (5 ml) was refluxed for 27 hours. To this mixture was added water, which was washed with ethyl ether, then was made acid with a 10% aqueous solution of potassium hydrogensulfate, followed by extraction with ethyl acetate. The extract solution was washed with a saline solution, and then dried (MgSO$_4$), followed by distilling off the solvent to leave the above-titled compound as colorless crystals (60 mg).

M.p. 298°–299° C. (recrystallized from ethyl acetate - isopropyl ether)

IR$\nu_{max}^{Nujol}$cm$^{-1}$: 1720, 1615, 1590, 1490, 1415, 1235

NMR(200MHz, CDCl$_3$)ppm: 2.11(3H,s), 2.24(2H,s), 2.39(3H,s),3.67(3H,s), 6.68(1H,s), 7.14–7.43(4H,m), 8.25(1H,s)

Using 2-benzoyl benzoic acids, reactions were allowed to proceed in a manner similar to that in Reference Example 1 to give compounds of Reference Examples 6–7.

REFERENCE EXAMPLE 6

7-Chloro-4-phenylisocoumarin-3-carboxylic acid

M.p. 220°–221° C.

REFERENCE EXAMPLE 7

4-(4-Fluorophenyl)-6-methylisocoumarin-3-carboxylic acid

M.p. 198°–199° C.

REFERENCE EXAMPLE 8

2-Amino-6-chloro-4-phenylisocoumarin

To a solution of the compound (1.0 g) obtained in Working Example 2 in dichloromethane (50 ml) was added trifluoroacetic acid (4 ml), which was stirred for 30 minutes at room temperature. The solvent was distilled off. To the residue was added ethyl acetate. The mixture was washed with an aqueous solution of sodium hydrogencarbonate and a saline solution, then dried (Na$_2$SO$_4$), followed by distilling off the solvent to afford the above-titled compound as yellow crystals (710 mg).

M.p. 216°–217° C. (recrystallized from ethyl acetate - isopropyl ether)

Elemental Analysis for C$_{15}$H$_{10}$NO$_2$Cl.1/4H$_2$O: Calcd.: C, 65.23; H, 3.83; N, 5.07; Found : C, 65.20; H, 3.97; N, 4.96

REFERENCE EXAMPLE 9

3-Amino-6-chloro-2-methyl-4-phenyl-1(2H)-isoquinoline

Using the compound (0.61 g) obtained in Working Example 5, a reaction was allowed to proceed in a manner similar to that of Reference Example 8 to afford the above-titled compound as yellow crystals (0.42 g).

M.p. 181°–183° C. (recrystallized from ethyl acetate - isopropyl ether)

Elemental Analysis for C$_{16}$H$_{13}$N$_2$OCl: Calcd.: C, 67,49; H, 4.60; N, 9.84; Found : C, 67.34; H, 4.69; N, 9.77

REFERENCE EXAMPLE 10

6-Fluoro-4-(4-fluorophenyl)isocoumarin-3-carboxylic acid

Starting from 2-(4-fluoro)benzoylbenzoic acid instead of 2-benzoyl-4-chlorobenzoic acid in Reference Example 1, a reaction was allowed to proceed in a manner like that of Reference Example 1, to afford the above-titled compound as colorless crystals.

M.p. 202°–205° C.

REFERENCE EXAMPLE 11

4-(2-Methoxyphenyl)-2-methyl-1(2H)-isoquinolinone-3-carboxylic acid

Starting from 4-(2-methoxyphenyl)isocoumarin-3-carboxylic acid (1.50 g), a reaction was allowed to proceed in a manner like that of Reference Example 2, using methylamine instead of ammonia in Reference Example 2, to afford the above-titled compound (1.34 g) as colorless crystals.

M.p. 205°–207° C.

REFERENCE EXAMPLE 12

4-(3,5-Di-t-butyl-4-hydroxyphenyl)-2-methyl-1(2H)-isoquinolinone-3-carboxylic acid

Step 1

N-[2-(3,5-Di-t-butyl-4-hydroxybenzoyl)benzoyl]-N-methyl glycine ethyl ester

To 2-(3,5-di-t-butyl-4-hydroxybenzoly)-benzoic acid (2.88 g) in tetrahydrofuran anhydride (80 ml) was added oxazolyl chloride (1.56 ml) and dimethylformamide (catalitic amount) and the mixture was stirred for 30 minutes. To the mixture was added triethylamine (1.15 ml) and the mixture was stirred for 2 hours at 50° C. The solvent was distilled off. To the residue were added anhydrous tetrahydrofuran (100 m;), sarcosine ethyl ester hydrochloride (3.75 g) and triethylamine (4.48 ml). The mixture was stirred for 15 hours at room temperature. The solvent was distilled off. To the redidue was added water and it was extracted with ethyl acetate. The extract solution was washed with dilute hydrochloric acid, an aqueous solution of sodium carbonate and water, successively, and then dried (Na$_2$SO$_4$). The solvent was distilled off to afford the above-titled compound as colorless crystals (2.0 g).

M.p. 98°–99° C. (recrystallized from ethyl acetate - isopropyl ether)

Step 2

4-(3,5-Di-t-butyl-4-hydroxyphenyl)-2-methyl-1-(2H)-isoquinolinone-3-carboxylic acid ethyl ester To a solution of the compound (1.85 g) obtained in Referance Example 2 in dimethylformamide (20 ml) was added sodium hydride (60% dispersion in mineral oil) (0.30 g) and chloromethyl methyl ether (1.60 ml). The mixture was stirred for 15 hours at room temperature. To the reaction mixture was added water, followed by extraction with ethyl acetate. The extract solution was washed and dried ($Na_2SO_4$), then the solvent was distilled off to leave a methoxymethyl ether derivative of the compound obtained in Step 1 as a colorless oily substance. To the oily substance were added anhydrous toluene (100 ml) and 1,8-diazacyclo[5.4.0]undec-7-ene (1.5 ml). The mixture was stirred for 4 hours at 110° C. To the reaction solution was added ethyl acetate and the mixture was washed with water, dilute hydrochloric acid and water, successively, then dried ($Na_2SO_4$), followed by distilling off the solvent to leave an oily substance containing 4-(3,5-di-t-butyl-4-methoxymethoxyphenyl)-3,4-dihydro-4-hydroxy-2-methyl-1(2H)-isoquinolinone-3-carboxylic acid ethyl ester (isolated as colorless crystals) as main ingredient. To the oily substance was added toluene (100 ml) and p-toluenesulfonic acid hydrate (1.0 g) and refluxed for 1 hour. To the mixture was added ethyl acetate and the mixture was washed with water, an aqueous solution of sodium hydrogencarbonate and water, successively, then dried ($Na_2SO_4$), followed by distilling off the solvent to afford the above-titled compound as pale yellow crystals (1.60 g).

M.p. 225°–227° C. (recrystallized from ethyl acetate-isopropyl ether)

Elemental Analysis for $C_{27}H_{33}NO_4$: Calcd.: C,74.45; H,7.64; N 3.22; Found : C,74.42; H,7.42; N,2.99

Step 3

4-(3,5-Di-t-butyl-4-hydroxyphenyl)-2-methyl-182H)-isoquinoline-3-carboxylic acid The compound (1.60 g) obtained in Step 2 was added ethanol (35 ml), $H_2O$ (7 ml) and potassium hydroxide (1.60 g) and refluxed for 24 hours. The solvent was distilled off. The residue was made acidic by adding diluted hydrochloric acid, followed by extraction with ethyl acetate. The extract solution was washed with water, then dried ($Na_2SO_4$), followed by distilling off the solvent to afford the above-titled compound as colorless crystals (1.60 g).

M.p. >300° C. (recrystallized from acetone-isopropyl ether)

Elemental Analysis for $C_{25}H_{29}NO_4 \cdot H_2O$: Calcd.: C,70.57; H,7.34; N,3.29; Found: C,70.71; H,7.60; N,3.40

REFERENCE EXAMPLE 13

4-Phenyl-1H-2-benzothiopyrane-3-carboxylic acid

Step 1

2-Bromomethylbenzophenone

A mixture of 2-methylbenzophenone (9.8 g), N-bromosuccinimide (8.9 g), benzoyl peroxide (0.5 g) and carbon tetrachloride (150 ml) was refluxed for 1 hour with light irradiation. The mixture was cooled, and then filtered to remove insoluble substances. The filtrate was concentrated to afford quantitatively the above-titled compound as an oily susbstance.

NMR (200MHz, $CDCl_3$) ppm: 4.70(2H,s), 7.26–7.65(7H,m), 7.75–7.85(2H,m)

Step 2

Ethyl ester of 2-benzoylbenzylthio acetic acid

To a solution of the compound obtained in Step 1 in dichloromethane (100 ml) were added ethyl ester of thioglycollic acid (6.0 g) and triethylamine (8.4 ml). The solution was stirred for 1.5 hour at room temperature, washed with water, then dried ($MgSO_4$), followed by distilling off the solvent. The residue was subjected to a silica gel column chromatography (hexane - ethyl acetate=9:1) to afford the above-titled compound as an oily susbstance (11.0 g).

NMR (200MHz, $CDCl_3$) ppm: 1.24(3H,t,J=7Hz), 3.04(2H,s), 4.03(2H,s), 4.12(2H,q,J=7Hz), 7.27–7.66(7H,m), 7.78–7.82(2H,m)

Step 3

Ethyl ester of 4-phenyl-1H-2-benzothiopyran-3-carboxylic acid

A solution of potassium-t-butoxide (7.14 g) in tetrahydrofuran (80 ml) was dropped into a solution of the compound obtained in Step 2 in tetrahydrofuran (30 ml), which was then stirred for 40 minutes at room temperature. The solvent was distilled off to half volume. To the solution was added water, followed by extraction with ethyl acetate. The ethyl acetate layer was washed with water and dried ($MgSO_4$), then the solvent was distilled off. The residue was crystallized from isopropyl ether-hexane to afford the above-titled compound as pale yellow crystals (0.75 g)

M.p. 89°–90° C. (recrystallized from ethanol)

Elemental Analysis for $C_{18}H_{16}O_2S$: Calcd.: C,72.94; H,5.44; Found: C,72.93; H,5.55

The aqueous layer was made acidic with 2N-HCl, followed by extraction with ethyl acetate. The extract solution was washed with water and dried ($MgSO_4$), then the solvent was distilled off to afford 4-phenyl-1H-2-benzothiopyran-3-carboxylic acid as colorless crystals (3.5 g).

M.p. 155°–156° C. (recrystallized from ethanol)

Elemental Analysis for $C_{16}H_{12}O_2S$: Calcd.: C, 71.62; H, 4.51; Found : C, 71.58; H,4.47

Step 4

4-Phenyl-1H-2-benzothiopyran-3-carboxylic acid

A mixture of ethyl ester of carboxylic acid (592 mg) obtained in Step 3, 2N-NaOH (3 ml), ethanol (2 ml), and dioxane (6 ml) was heated for 1 hour at 80° C. To the mixture was added water, then the mixture was made acidic with 2N-HCl, followed by extraction with ethyl acetate. The extract solution was washed with water and dried ($MgSO_4$), then the solvent was distilled off. The residue was crystallized from isopropyl ether-hexane to afford the above-titled compound as colorless crystals.

M.p. 155°–156° C.

The compound was the same as the carboxylic acid obtained in Step 3.

REFERENCE EXAMPLE 14

4-(2-Methoxyphenyl)-1H-2-benzothiopyran-3-carboxylic acid

Step 1

Ethyl ester of 2-(2-methoxybenzoyl)benzylthio acetic acid

Using 2-methoxy-2'-methylbenzophenone, reaction was allowed to proceed in a manner similar to that in Step 1 and Step 2 of Reference Example 13 to give the above-titled compound as an oily substance.

NMR(200MHz, CDCl$_3$) ppm: 1.25(3H,t,J=8Hz), 3.10(2H,s), 3.67(3H,s), 4.16(2H,s), 4.16(2H,q,J=8Hz), 6.94–7.06(2H,m), 7.20–7.53(6H,m)

Step 2

Ethyl ester of 4-(2-methoxyphenyl)-1H-2-benzothiopyran-3-carboxylic acid

A solution of diisopropylamine (2.1 ml) in tetrahydrofuran (20 ml) was added dropwise to a solution of n-butyllithium in hexane (1.6mmol/ml, 8.5 ml) at −78° C. The mixture was stirred for 30 minutes at −78° C. and added dropwise to a solution of the compound obtained in Step 1 in tetrahydrofuran (5 ml). The mixture was stirred for 30 minutes at −78° C. and made acidic by adding 2N-HCl, followed by extraction with ethyl acetate. The ethyl acetate layer was washed with water and dried (MgSO$_4$), then the solvent was distilled off to afford the ethyl ester of 3,4-dihydro-4-hydroxy-4-(2-methoxyphenyl)-1H-2-benzothiopyran-3-carboxylic acid as an oily substance. The oily substance was dissolved in benzene, and p-tluenesulfonic acid hydrate (0.77 g) was added, then the solution was refluxed with a Dean-Stark system. After 30 minutes to the mixture was added water, followed by extraction with ethyl acetate. The extract solution was washed with water, and dried (MgSO$_4$), followed by distilling off the solvent. The residue was subjected to a silica gel column chromatography (hexane - ethyl acetate=4:1) to afford the above-titled compound as a colorless crystals (0.77 g).

M.p. 86°–87° C. (recrystallized from ethanol)

Elemental Analysis for C$_{19}$H$_{19}$O$_3$S: Calcd.: C, 69.91; H, 5.56; Found : C, 70.00; H, 5.69

Step 3

4-(2-Methoxyphenyl)-1H-2-benzothiopyran-3-carboxylic acid

Using the compound obtained in Step 2, reaction was allowed to proceed in a manner of Step 4 of Reference Example 13 to give the above-titled compound as a colorless crystal.

M.p. 190°–192° C.

Elemental Analysis for C$_{17}$H$_{14}$O$_3$S: Calcd.: C, 68.44; H, 4.73; Found : C, 68.48; H, 4.81

WORKING EXAMPLE 1

N-(6-Chloro-4-phenylisocoumarin-3-yl)-N'-(2,4-difluorophenyl)urea

To a mixture of 6-chloro-4-phenylisocoumarin-3-carboxylic acid (1.50 g), diphenyl phosphoryl azide (DPPA) (1.43 ml) and benzene (50 ml) was added dropwise triethylamine (0.71 ml) while stirring at room temperature. This mixture was stirred for one hour at room temperature and for 30 minutes under reflux, then there was added 2,4-difluoroaniline (0.80 ml), followed by refluxing for 2 hours. The reaction mixture was cooled, and then washed with water, diluted hdyrochloric acid, an aqueous solution of sodium hydrogencarbonate and water, successively, then dried (Na$_2$SO$_4$), followed by distilling off the solvent. The residue was subjected to a silica gel column chromatography (hexane-acetone=4:1) to afford the above-titled compound as colorless crystals (0.90 g).

M.p. 196°–197° C. (recrystallized from ethyl acetate - isopropyl ether)

Elemental Analysis for C$_{22}$H$_{13}$N$_2$O$_3$ClF$_2$: Calcd.: C, 61.91; H, 3.07; N, 6.56; Found : C, 62.03; H, 3.20; N, 6.44

WORKING EXAMPLE 2 t-Butyl N-(6-chloro-4-phenylisocoumarin-3-yl) carbamate

A mixture of 6-chloro-4-phenylisocoumarin-3-carboxylic acid (2.50 g), t-butanol (30 ml), DPPA (2.35 ml) and triethylamine (1.18 ml) was stirred for one hour at room temperature, followed by refluxing for one hour. The reaction mixture was concentrated. To the concentrate was added ethyl acetate. This mixture was washed with water, diluted hydrochloric acid, an aqueous solution of sodium hydrogencarbonate and water, successively, followed by drying (Na$_2$SO$_4$). The solvent was distilled off to afford the above-titled compound as colorless crystals (1.52 g).

M.p. 183°–184° C. (recrystallized from ethyl acetate - isopropylether)

Elemental Analysis for C$_{20}$H$_{18}$NO$_4$Cl: Calcd : C, 64.61; H, 4.88; N, 3.77; Found : C, 64.36; H, 5.12; N, 3.60

WORKING EXAMPLE 3

N-[6-Chloro-1,2-dihydro-2-methyl-4-phenyl-1-oxoisoquinolin-3-yl]-N'-(2,4-difluorophenyl)urea Using 6-chloro-2-methyl-4-phenyl-1(2H)-isoquinolinone-3-carboxylic acid instead of 6-chloro-4-phenylisocoumarin-3-carboxylic acid, the reaction was allowed to proceed in the manner that of Working Example 1 to afford the above-titled compound as colorless crystals.

M.p.>300° C.

Elemental Analysis for C$_{23}$H$_{16}$N$_3$O$_2$ClF$_2$: Calcd.: C, 62.81; H, 3.67; N, 9.55; Found: C, 62.82; H, 3.57; N, 9.46

WORKING EXAMPLE 4

N-[6-Chloro-1,2-dihydro-2-methyl-4-phenyl-1-oxoisoquinolin-3-yl]-N'-(3-methylphenyl)urea By using 6-chloro-2-methyl-4-phenyl-1(2H)-isoquinolinone-3-carboxylic acid and 3-methyl aniline respectively in place of 6-chloro-4-phenylisocoumarin-3-carboxylic acid and 2,4-difluoroaniline in Working Example 1, reaction was allowed to proceed in a manner like that of Working Example 1 to afford the above-titled compound as colorless crystals.

M.p.>300° C.

Elemental Analysis for C$_{24}$H$_{20}$N$_3$O$_2$Cl: Calcd.: C, 68.98; H, 4.82; N, 10.06; Found : C, 68.87; H, 4.94; N, 9.84

WORKING EXAMPLE 5 t-Butyl N-(6-chloro-1,2-dihydro-2-methyl-4-phenyl-1-oxoisoquinolin-3-yl)carbamate By using 6-chloro-2-methyl-4-phenyl-1(2H)-isoquinolinon-3-carboxylic acid in place of 6-chloro-4-phenylisocoumarin-3-carboxylic acid in Working Example 2, the reaction was allowed to proceed in a manner like that of Working Example 2 to afford the above-titled compound as colorless crystals.

M.p. 217°–218° C.

Elemental Analysis for $C_{21}H_{21}N_2O_3Cl$: Calcd.: C, 65.54; H, 5.50; N, 7.28; Found : C, 68.87; H, 4.94; N, 7.06

Using 4-phenyl-1(2H)-isoquinolinon-3-carboxylic acid, reactions were allowed to proceed in a manner like that of Working Example 3 to afford compounds of Working Examples 6–8.

WORKING EXAMPLE 6

N-(6-Chloro-1,2-dihydro-4-phenyl-1-oxoisoquinolin-3-yl)-N'-(2,4-difluorophenyl)urea M.p. >300° C.

WORKING EXAMPLE 7

N-[1,2-Dihydro-4-(4-fluorophenyl)-2-methyl-1-oxoisoquinolin-3-yl]-N'-(2,4-difluorophenyl)urea M.p. >300° C.

WORKING EXAMPLE 8

N-[1,2-Dihydro-4-(2-methylphenyl)-2,6,7-trimethyl-1-oxoisoquinolin-3-yl]-N'-(2,4-difluorophenyl)urea M.p. 252°–254° C.

In a manner like that of Working Example 1, 4-phenylisocoumarin-3-carboxylic acids were allowed to react with DPPA, then the reaction products were further allowed to react with amines to afford compounds of Working Examples 9–20.

WORKING EXAMPLE 9

N-(7-Chloro-4-phenylisocoumarin-3-yl)-N'-(2,4-difluorophenyl)urea

M.p. 194°–195° C.

WORKING EXAMPLE 10

N-[4-(4-Fluorophenyl)-6-methylisocoumarin-3-yl]-N'-(2,4-difluorophenyl)urea

M.p. 246°–248° C.

WORKING EXAMPLE 11

N-[4-(4-Fluorophenyl)isocoumarin-3-yl]-N'-(2,4-difluorophenyl)urea

M.p. 204°–205° C.

WORKING EXAMPLE 12

N-(4-Phenylisocoumarin-3-yl)-N'-(2,4-difluorophenyl)urea

M.p. 194°–195° C.

WORKING EXAMPLE 13

N-(6-Chloro-4-phenylisocoumarin-3-yl)-N'-(4-acetoxy-3,5-dimethylphenyl)urea

M.p. 218°–219° C.

WORKING EXAMPLE 14

N-[4-(2-Methoxyphenyl)isocoumarin-3-yl]-N'-(4-acetoxy-3,5-dimethylphenyl)urea

M.p. 224°–225° C.

WORKING EXAMPLE 15

N-[4-(2-Methoxyphenyl)isocoumarin-3-yl]-N'-(2,4difluorophenyl)urea

M.p. 213°–215° C.

WORKING EXAMPLE 16

N-[6-Fluoro-4-(4-fluorophenyl)isocoumarin-3-yl]-N'-(2,4-difluorophenyl)urea

M.p. 191°–193° C.

WORKING EXAMPLE 17

N-[6-Fluoro-4-(4-fluorophenyl)isocoumarin-3-yl]-N'-(4-acetoxy-3,5-dimethyl phenyl)urea M.p. 233°–234° C.

WORKING EXAMPLE 18

N-(4-Isocoumarin-3-yl)-N'-(4-acetoxy-3,5-dimethylphenyl)urea

M.p. 223°–225° C.

WORKING EXAMPLE 19

N-[4-(2-Methoxyphenyl)isocoumarin-3-yl]-N'-cyclohexylurea

M.p. 217°–219° C.

WORKING EXAMPLE 20

N-[4-(2-Methoxyphenyl)isocoumarin-3-yl]-N'-ethoxycarbonyl-methylurea

M.p. 155°–157° C.

WORKING EXAMPLE 21

Benzyl N-[4-(2-methoxyphenyl)isocoumarin-3-yl]carbamate

A mixture of 4-(2-methoxyphenyl)isocoumarin-3-carboxylic acid (148 mg), dried benzene (8 ml), DPPA(0.143 ml) and triethylamine (0.071 ml) was stirred for 1 hour at room temperature and refluxed for 30 minutes. To the mixture was added benzyl alchol (0.15 ml), and the mixture was refluxed for 4 hours. The solution was cooled, and washed with water, dilute hydrochloric acid, an aqueous solution of sodium hydrogencarbonate and water, successively, and then dried (MgSO$_4$), followed by distilling off the solvent. The residue was subjected to silica gel colum chromatography (hexane - acetone=3:1) to give the above-titled compound as colorless crystals (50 mg).

M.p. 144°–146° C. (recrystallized from ethyl acetate-ethyl ether)

Elemental Analysis for $C_{24}H_{19}NO_5$: Calcd.: C, 71.81; H, 4.77: N, 3.49; Found : C, 71.64; H, 4.52; N, 3.57

WORKING EXAMPLE 22 t-Butyl N-[4-(2-methoxyphenyl)isocoumarin-3-yl]carbamate

By using 4-(2-methoxyphenyl)isocoumarine-3-carboxylic acid instead of 6-chloro-4-phenylisocoumarin-3-carboxylic acid in Working Example 2, a reaction was allowed to proceed in a manner similar to that of Reference Example 2 to afford the above-titled compound as colorless crystals.

M.p. 203°–205° C. (recrystallized from acetone-ethyl ether)

Elemental Analysis for $C_{21}H_{21}NO_5$: Calcd.: C, 68.65; H, 5.76; N, 3.81; Found : C, 68.42; H, 5.48; N, 3.83

WORKING EXAMPLE 23

N-[4-(3,5-Di-t-butyl-4-hydroxyphenyl)-1,2-dihydro-2-methyl-1-oxoisoquinolin-3-yl-]-N'-(2,4-difluorophenyl-)urea By using isoquinolinone-3-carboxylic acid obtained in Reference Example 12, reaction was allowed to proceed in a manner like that of Working Example 3 to afford the above-titled compound as colorless crystals.

M.p. 230°–232° C.

WORKING EXAMPLE 24

N-[4-(2-Methoxyphenyl)-1,2-dihydro-2-methyl-1-oxoisoquinolin-3-yl]-N'-(2,4-difluorophenyl)urea By using isoquinolinone-3-carboxylic acid obtained in Reference Example 11, a reaction was allowed to proceed in a manner like that of Working Example 3 to afford the above-titled compound as colorless crystals.

M.p. 207°–209° C.

WORKING EXAMPLE 25

N-[4-(2-Methoxyphenyl)-1,2-dihydro-2-methyl-1-oxoisoquinolin-3-yl]-N'-ethoxycarbonylmethylurea By using the compound obtained in Reference Example 11 and the ethyl ester of glycine respectively in place of 6-chloro-4-phenylisocoumarin and 2,4-difluoroaniline in Working Example 1, the reaction was allowed to proceed in a manner like that of Working Example 1 to afford the above-titled compound as colorless crystals.

M.p. 128°–130° C.

WORKING EXAMPLE 26

N-(4-acetoxy-3,5-dimethylphenyl)-N'-(4-phenyl-1H-2-benzothiopyran-3-yl)urea

To a mixture of 4-phenyl-1H-2-benzothiopyran-3-carboxylic acid (in Reference Example 13) (268 mg), DPPA (330 mg) and benzene (5 ml) was added dropwise to triethylamime (0.14 ml) and the mixture was stirred at room temperature for 30 minutes, then refluxed for 30 minutes. To the mixture were added 4-acetoxy-3,5-dimethylaniline hydrochloride (258 mg) and triethylamine (0.17 ml), followed by refluxing for 20 minutes. The mixture was washed with water, then dried (MgSO$_4$), followed by distilling off the solvent. To the residue was added ether to afford the above-titled compound as colorless crystals (280 mg).

M.p. 206°–208° C. (recrystallized from ethanol-dichloromethane)

Elemental Analysis for $C_{26}H_{24}N_2O_3$: Calcd.: C, 70.25; H, 5.44; N, 6.30; Found : C, 69.93; H, 5.21; N, 6.11

WORKING EXAMPLE 27

N-(4-Acetoxy-3,5-dimethylphenyl)-N'-[4-(2-methoxyphenyl)-1H-2-benzothiopyran-3-yl]urea By using the compound obtained in Reference Example 14, the reaction was allowed to proceed in a manner like that of Working Example 26 to afford the above-titled compound.

M.p. 207°–209° C. (recrystallized from acetone)

Elemental Analysis for $C_{27}H_{26}N_2O_4$: Calcd.: C, 68.33; H, 5.52; N, 5.90; Found : C, 68.38; H, 5.34; N, 5.98

WORKING EXAMPLE 28

N-(4-Dimethylaminophenyl)-N'-[4-(2-methoxyphenyl)-1H-2-benzothiopyran-3-yl]urea

By using 4-(2-methoxyphenyl)-1H-2-benzothiopyran-3-carboxylic acid and 4-N,N-dimethylaminoaniline in place of 4-phenyl-1H-2-benzothiopyran in Working Example 26 and 4-acetoxy-3,5-dimethylaniline, respectively, the reaction was allowed to proceed in a manner like that of Working Example 26 to afford the above-titled compound.

M.p. 128°–130° C. (recrystallized from acetone)

Elemental Analysis for $C_{25}H_{25}N_3O_2S$: Calcd.: C, 69.58; H, 5.84; N, 9.74; Found : C, 69.69; H, 5.80; N, 9.74

WORKING EXAMPLE 29

N-(4-Hydroxy-3,5-dimethylphenyl)-N'-(4-phenyl-1H-2-benzothiopyran-3-yl)urea

A solution of compound obtained in Working Example 26 (80 mg) in methanol-tetrahydrofuran (1:1, 3 ml) was added with 2N-NaOH (1 ml) and then the mixture was stirred for 15 minutes at room temperature. To the solution was added water, and made acidic with 2N-HCl, followed by extraction with ethyl acetate. The extact solution was washed with water and dried (MgSO$_4$), then the solvent was distilled off. To the residue was added acetone to afford the above-titled compound as colorless crystals (32 mg).

M.p. 227°–228° C.

Elemental Analysis for $C_{24}H_{22}N_2O_2S$: Calcd.: C, 71.62; H, 5.51; N, 6.96; Found : C, 71.37; H, 5.53; N, 7.04

WORKING EXAMPLE 30

N-(4-N,N-dimethylaminophenyl)-N'-(6-chloro-4-phenylisocoumarin-3-yl)urea

By using 4-N,N-dimethylaminoaniline instead of 2,4-difluoroaniline in Working Example 1, the reaction was allowed to proceed in a manner like that of Working Example 1 to afford the above-titled compound as colorless crystals.

M.p. 210°–212° C.

WORKING EXAMPLE 31

N-(4-N,N-dimethylaminophenyl)-N-[4-(2-methoxyphenyl)isocoumarin-3-yl]urea

By using 4-(2-methoxyphenyl)isocoumarin-3-carboxylic acid and 4-N,N-dimethylaminoaniline in place of 6-chloro-4-phenylisocoumarine-3-carboxylic acid and 2,4-difluoroaniline in Working Example 1, respectively, the reaction was allowed to proceed in a manner like that of Working Example 1 to afford the above-titled compounds as colorless crystals.

M.p. 229°–231° C. (recrystallized from acetone)

What we claim is:

1. A compound of the formula:

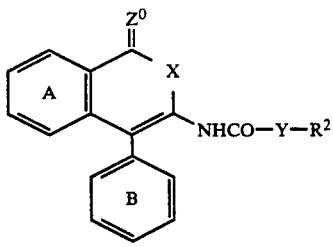

wherein ring A and ring B stand independently for a benzene ring which may be substituted with 1 to 4 substituents selected from the group consisting of (1) a halogen, (2) a $C_{1-6}$ alkyl group which may be substituted with 1 to 5 halogens, (3) a $C_{1-6}$ alkoxy group which may be substituted with 1 to 5 halogens, (4) a $C_{1-6}$ alkylthio group which may be substituted with 1 to 5 halogens, (5) a $C_{1-7}$ acylamino group, (6) a $C_{1-3}$ acyloxy group and (7) a hydroxyl group, or adjacent carbon atoms on the ring A or B may form a 5- to 7-membered ring together with a group of the formula: $-(CH_2)_r-$ wherein r denotes an integer of 3 to 5, $Z^0$ stands for O or S or

stands for $-CH_2-$, X stands for O, S or $NR^1$ wherein $R^1$ stands for a hydrogen atom or a $C_{1-6}$ alkyl group; Y stands for NH, O or $(CH_2)_n$ wherein n denotes 0 to 2; and $R^2$ stands for a hydrocarbon group selected from the group consisting of (1) a straight-chain or branched $C_{1-8}$ alkyl group, (2) a $C_{3-8}$ cycloalkyl group, (3) a $C_{3-8}$ cycloalkyl-$C_{1-4}$ alkyl group, (4) a $C_{6-10}$ aryl group of (5) a $C_{7-16}$ aralkyl group, each of which may be substituted with 1 to 4 substituents selected from the group consisting of (i) a halogen, (ii) a $C_{1-6}$ alkyl group which may be substituted with 1 to 5 halogens, (iii) a $C_{1-6}$ alkoxy group which may be substituted with 1 to 5 halogens, (iv) a $C_{1-6}$ alkylthio group which may be substituted with 1 to 5 halogens, (v) a $C_{1-7}$ acylamino group, (vi) a $C_{1-3}$ acyloxy group, (vii) a hydroxyl group and (viii) an amino group which may be substituted with one or two $C_{1-4}$ alkyl groups, or a pharmaceutically acceptable salt thereof.

2. A compound of the formula:

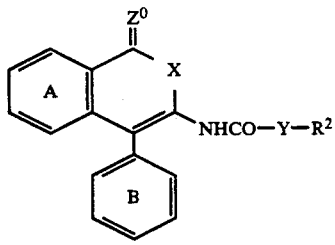

wherein ring A and ring B stand independently for a benzene ring which may be substituted with 1 to 4 substituents selected from the group consisting of (1) a halogen, (2) a $C_{1-6}$ alkyl group which may be substituted with 1 to 5 halogens, (3) a $C_{1-6}$ alkoxy group which may be substituted with 1 to 5 halogens, (4) a $C_{1-6}$ alkylthio group which may be substituted with 1 to 5 halogens, (5) a $C_{1-7}$ acylamino group, (6) a $C_{1-3}$ acyloxy group and (7) a hydroxyl group, or adjacent carbon atoms on the ring A or B may form a 5- or 7-membered ring together with a group of the formula: $-(CH_2)_r-$ wherein r denotes an integer of 3 to 5, Z stands for O or S, X stands for O, S or $NR^1$ wherein $R^1$ stands for a hydrogen atom or a $C_{1-6}$ alkyl group; Y stands for NH, O or $(CH_2)_n$ wherein n denotes 0 to 2; and $R^2$ stands for a hydrocarbon group selected from the group consisting of (1) a straight-chain or branched $C_{1-8}$ alkyl group, (2) a $C_{3-8}$ cycloalkyl group, (3) a $C_{3-8}$ cycloalkyl-$C_{1-4}$ alkyl group, (4) a $C_{6-10}$ aryl group or (5) a $C_{7-16}$ aralkyl group, each of which may be substituted with 1 to 4 substituents selected from the group consisting of (i) a halogen, (ii) a $C_{1-6}$ alkyl group which may be substituted with 1 to 5 halogens, (iii) a $C_{1-6}$ alkoxy group which may be substituted with 1 to 5 halogens, (iv) a $C_{1-6}$ alkylthio group which may be substituted with 1 to 5 halogens, (v) a $C_{1-7}$ acylamino group, (vi) a $C_{1-3}$ acyloxy group, (vii) a hydroxyl group and (viii) an amino group which may be substituted with one or two $C_{1-4}$ alkyl groups, or a pharmaceutically acceptable salt thereof.

3. A compound as claimed in claim 1, wherein the ring A and the ring B stand independently for a benzene ring which may be substituted with 1 to 4 substituents selected from the group consisting of (1) a halogen, (2) a $C_{1-6}$ alkyl group which may be substituted with 1 to 3 halogens and (3) a $C_{1-4}$ alkoxy group which may be substituted with 1 to 3 halogens.

4. A compound as claimed in claim 1, wherein $R^1$ is hydrogen, a straight-chain or branched $C_{1-6}$ alkyl group, a $C_{3-6}$ cycloalkyl group or a $C_{3-6}$ cycloalkyl-$C_{1-4}$ alkyl group.

5. A compound as claimed in claim 1, wherein X stands for O or S.

6. A compound as claimed in claim 1, wherein Y stands for O or NH.

7. A compound as claimed in claim 1, wherein $R^2$ stands for (1)a $C_{1-8}$ alkyl group, (2)a $C_{3-8}$ cycloalkyl group (3)a $C_{6-10}$ aryl group or (4)a $C_{7-16}$ aralkyl group, each of which may be substituted with 1 to 4 substituents selected from the group consisting of (i)a halogen, (ii)a $C_{1-6}$ alkyl group which may be substituted with 1 to 5 halogens, (iii)a $C_{1-6}$ alkoxy group which may be substituted with 1 to 5 halogens, (iv)a $C_{1-6}$ alkylthio group which may be substituted with 1 to 5 halogens, (v)a $C_{1-7}$ acylamino group, (vi)a $C_{1-3}$ acyloxy group and (vii)a hydroxyl group.

8. A compound as claimed in claim 1, wherein $R^2$ stands for (1)a $C_{1-6}$ alkyl group, (2)a $C_{3-8}$ cycloalkyl group, (3)a phenyl group or (4)a phenyl-$C_{1-4}$ alkyl group, each of which may be substituted with 1 to 3 substituents selected from the group consisting of (i)a halogen, (ii)a $C_{1-4}$ alkyl group, (iii)a $C_{1-4}$ alkoxy group, (iv)a $C_{1-3}$ acyloxy group and (v)an amino group which may be substituted with one or two $C_{1-4}$ alkyl groups.

9. A compound as claimed in claim 1, wherein $R^2$ stands for (1)a $C_{1-6}$ alkyl group, (2)a $C_{5-8}$ cycloalkyl group, (3)a phenyl group which may be substituted with 1 to 3 substituents selected from the group consisting of (i)a halogen, (ii)a $C_{1-4}$ alkyl group, (iii)a $C_{1-4}$ alkoxy group, (iv) a $C_{1-3}$ acyloxy group and (v)an amino group which may be substituted with one or two $C_{1-4}$ alkyl groups, or (4)a phenyl-$C_{1-4}$ alkyl group.

10. A compound as claimed in claim 1, wherein $Z^0$ stands for O or

stands for —CH$_2$—, the ring A and the ring B stand independently for a benzene ring which may be substituted with 1 or 2 substituents selected from the group consisting of (1) a halogen, (2) a C$_{1-6}$ alkyl group and (3) a C$_{1-4}$ alkoxy and R$^1$ stands for hydrogen atom or a C$_{1-4}$ alkyl group.

11. A compound as claimed in claim 1 which is N-(6-chloro-4-phenylisocoumarin-3-yl)-N'-(2,4-difluorophenyl)urea.

12. A compound as claimed in claim 1 which is N-[4-(4-fluorophenyl)-6-methylisocoumarin-3-yl]-N'-(2,4-difluorophenyl)urea.

13. A compound as claimed in claim 1 which is N-(6-chloro-4-phenylisocoumarin-3-yl)-N'-(4-acetoxy-3,5-dimethylphenyl)urea.

14. A compound as claimed in claim 1 which is N-[4-(2-methoxyphenyl)isocoumarin-3-yl]-N'-(4-acetoxy-3,5-dimethylphenyl)urea.

15. A compound as claimed in claim 1 which is N-[4-(2-methoxyphenyl)isocoumarin-3-yl]-N'-(2,4-difluorophenyl)urea.

16. A compound as claimed in claim 1 which is N-[4-(2-methoxyphenyl)isocoumarin-3-yl]-N'-cyclohexylurea.

17. A compound as claimed in claim 1 which is N-(4-acetoxy-3,5-dimethylphenyl)-N'-[4-(2-methoxyphenyl)-1H-2-benzothiopyran-3-yl]urea.

18. A compound as claimed in claim 1 which is N-(4-hydroxy-3,5-dimethylphenyl)-N'-(4-phenyl-1H-2-benzothiopyran-3-yl]urea.

19. An acyl CoA:cholesterol transferase inhibitor composition which comprises an effective inhibiting amount of a compound of the formula:

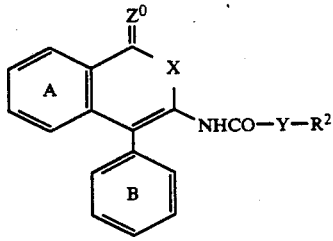

wherein the symbols are the same meaning as defined in claim 1, or a pharmaceutically acceptable salt thereof and a pharmacologically acceptable carrier.

20. A method for inhibiting acyl CoA: cholesterol transferase in a mammal in need which comprises administering an effective amount of a compound as claimed in claim 1 or a pharmaceutically acceptable salt thereof.

* * * * *